United States Patent [19]

Satoh et al.

[11] 4,227,809

[45] Oct. 14, 1980

[54] METHOD OF DETECTING FLAWS ON THE SURFACE OF METAL

[75] Inventors: Masakazu Satoh, Mito; Miyuki Igarashi; Shigeo Senoo, both of Ibaraki, all of Japan

[73] Assignee: Doryokuro Kakunenryo Kaihatsu Jigyodan, Tokyo, Japan

[21] Appl. No.: 945,070

[22] Filed: Sep. 22, 1978

[30] Foreign Application Priority Data

Sep. 30, 1977 [JP] Japan ................. 52/116698

[51] Int. Cl.³ ............................................. G01N 21/00
[52] U.S. Cl. ..................................... 356/237; 356/446
[58] Field of Search ................ 356/445, 446, 237; 250/562, 563, 572

[56] References Cited

U.S. PATENT DOCUMENTS 3,702,737  11/1972  Mottier ........................ 356/237 X
3,792,268  2/1974   Bjerke et al. ................. 356/446 X
3,931,525  1/1976   Clarke .......................... 250/572

Primary Examiner—John K. Corbin
Assistant Examiner—Matthew W. Koren
Attorney, Agent, or Firm—Wenderoth, Lind & Ponack

[57] ABSTRACT

A method of detecting minute flaws on the surface of a metal material is provided, which is constituted by the steps of directing a laser beam onto the surface of the metal material, reflecting a component of the beam directly reflected by the surface of the material by a reflector having a rough surface, and measuring the change in the quantity of light in the beam reflected by said reflector. Alternatively, a component of the laser beam directly reflected by the surface of the material and a component of the laser beam scattered by the metal surface are passed through a semitransparent filter having a rough surface, and the change in the quantity of light in the beam passed through the filter is measured.

6 Claims, 5 Drawing Figures

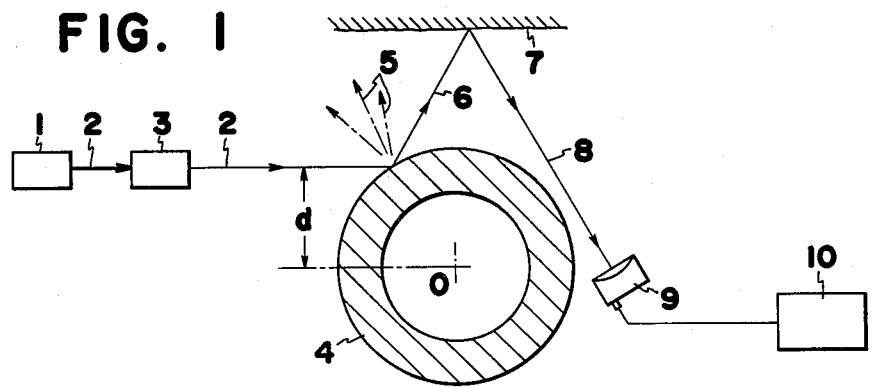
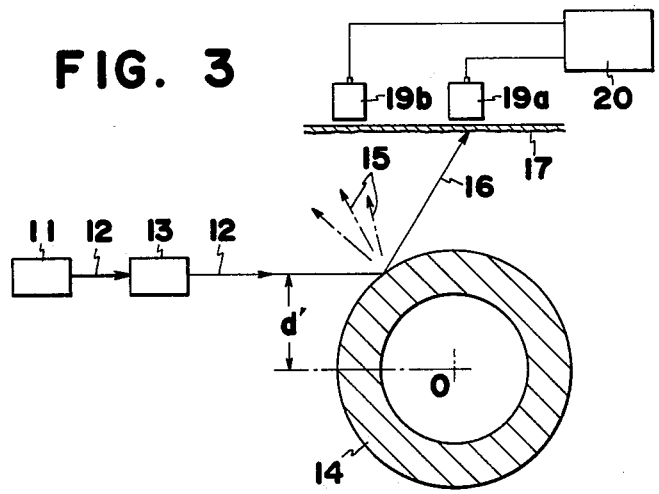
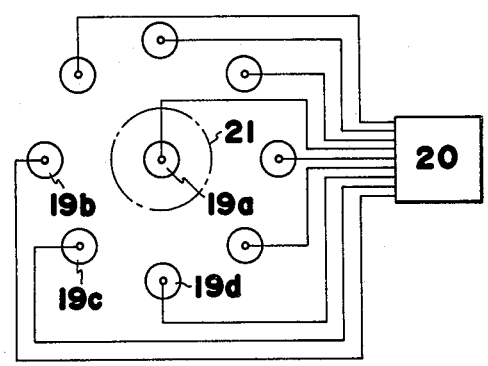

METHOD OF DETECTING FLAWS ON THE SURFACE OF METAL

BACKGROUND OF THE INVENTION

The present invention relates to a method of detecting minute flaws on the surface of a metal material, which comprises directing a collimated laser beam on the surface of the metal material, and measuring the change in quantity of light from the beam which is reflected or scattered by the metal surface.

When a laser beam is directed onto the surface of a metal material, a distribution of bright points which is called a speckle pattern occurs due to the interference with the reflected beam. The shape, size and type of flaws on the outer surface of the metal material to be inspected can be detected by measuring and analyzing the speckle pattern. Namely, when a finely collimated laser beam is spot-directed or scan-directed onto the surface of the metal material at a predetermined angle, the quantity of light from the reflected beam which forms a speckle pattern is reduced because it is scattered by the metal surface when flaws exist thereon.

According to a conventional method, the laser beam reflected by the surface of the metal to be inspected is directly put into a light detector through a lens or it is separated by a mirror and then put into a light detector, so as to measure the amount of decrease in intensity of the light due to the scattering of the reflected laser beam. (See, for example, "Iron and Steel Engineer", pages 67 to 70, June 1974.) However, since a speckle pattern includes information on the details of the surface condition of a sound portion of the surface to be inspected, the result of the measurment is seriously affected by changes in the condition of a sound portion thereof, or by the vibration of the surface to be inspected which occurs when the metal material to be inspected is moving. Thus, the flaw-detecting capability of the conventional method is extremely low. When the scattered component of the laser beam is detected by a conventional method, an image formed by the scattered beam due to a flaw may be very sharp and may be positioned in a limited space. Thus, flaws oriented in a certain direction may not be detected at all.

SUMMARY OF THE INVENTION

An object of the present invention is to eliminate the drawbacks encountered in the conventional method.

Another object of the present invention is to provide a method of detecting the flaws on the surface of a metal material with a high accuracy without any influence due to the change in the surface condition of a sound portion of the surface and due to the vibration of the surface occurring while the metal material is moving.

According to the present invention, there is provided a method of detecting flaws on the surface of a metal material comprising: directing a laser beam onto the surface of the metal material to be inspected so as to vary the position of irradiation; reflecting by a reflector having a rough surface a component of the beam which is directly reflected by said surface of the metal material; and measuring the change in the quantity of light from the beam reflected by said reflector.

Furthermore, according to the present invention, there is also provided a method of detecting flaws on the surface of a metal material comprising: directing a laser beam onto the surface of the metal material to be inspected so as to vary the position of irradiation; passing a component of the beam which is directly reflected by the metal surface and a component of the beam which is directly scattered by the metal surface through a semitransparent filter having a rough surface and measuring the change in quantity of light of at least one of said component of the beam reflected by said metal surface and passing through said filter and said component of the beam scattered by said metal surface and passing through said filter.

Thus, in the method according to the present invention, the intensity of the beam from the surface of the metal to be inspected is leveled by an optical means. The optical means can be one of two types, i.e. a reflection means in which a reflecting screen having a rough surface is used, and a filtering means in which a semitransparent filtering screen having a rough surface is used.

Other objects and advantages of the present invention will become apparent as the invention becomes better understood by reference to the following description of the preferred embodiments when considered in conjunction with the accompanying drawings.

BRIEF DESCRIPTION OF THE DRAWINGS

FIG. 1 is a schematic diagram of an embodiment of the method according to the present invention;

FIG. 2 is an example of an output signal from the photoelectric converter shown in FIG. 1;

FIG. 3 is a schematic diagram of a different embodiment of the method according to the present invention;

FIG. 4 is an example of an output signal from a photoelectric converter 19b shown in FIG. 3; and FIG. 5 shows an example of an arrangement of a plurality of photoelectric converters.

DESCRIPTION OF THE PREFERRED EMBODIMENT

FIG. 1 is a schematic diagram of an embodiment for carrying out the reflection type method according to the present invention.

Laser beam 2 from a laser oscillater 1 is finely collimated by an optical system 3 consisting of a lens or the like, and then directed onto the surface of a metal material 4 to be inspected. In this embodiment, the metal material 4 to be inspected is tubular, for example, a fuel cladding tube for nuclear reactors, and the laser beam 2 is directed onto a portion of the surface of the material 4 that is spaced perpendicularly from the axis thereof a predetermined distance d. The eccentricity d is a specifically determined value for the detection of flaws on the surface of the cross-sectionally circular material 4 and for the separation of the scattered component 5 of the beam from a directly reflected component 6 of the beam 6. The component 6 of the laser beam 2 reaches a reflecting screen 7. The reflecting surface of the reflecting screen 7 is comparatively rough so as to level the component 6 of the reflected beam and reflect it again. As the reflecting screen 7, thin paper which may be semitransparent or opaque can be used. The beam 6 thus scattered by the reflecting screen 7 and leveled thereby further advances as a reflected beam 8, which is then converted into an electric signal by a photoelectric converter 9. The electric signal is treated by a suitable signal treating means 10.

The quantity of light in the reflected beam 8 is measured while gradually changing the position of impingement of the laser beam 2 on the surface of the material 4, to detect the existence and position of flaws thereon.

In order to change the position of impingement of laser beam 2 on the material 4, the material 4 may be rotationally moved, the laser beam 2 may be scan-directed, or a combination of these operations may be used.

FIG. 2 shows an example of an output signal from the photoelectric converter 9.

In the above-described embodiment, the metal material 4 to be inspected is tubular but, needless to say, the method according to the present invention can also be applied to a flat metal material, etc. When a flat metal material is inspected, the reflecting screen may be inclined to separate the scattered component of the beam from the directly reflected component.

Thus, according to the reflection method of the present invention, flaws on the surface of a metal material of any shape can be detected by reflecting the component of the laser beam reflected by the surface of the material to level the distribution of intensity in the reflected beam, without any influence by the changes of the surface condition in the sound portion of the material.

FIG. 3 shows an embodiment for carrying out the filtering method according to the present invention. This embodiment is shown as being used with a cylindrical metal material 14 just as the embodiment shown in FIG. 1 but it can, of course, be applied to a flat metal meterial.

Laser beam 12 from a laser oscillator 11 is finely collimated by an optical system 13 and directed onto the surface of a metal pipe 14 to be inspected. The laser beam 12 is directed in the same manner as in the embodiment shown in FIG. 1, i.e. on the position on a surface of the material 14 which is spaced perpendicularly from the axis thereof a distance d', to separate a scattered component 15 from a direcly reflected component 16, which then advances toward a semitransparent filtering screen 17 having a rough surface. As the filtering screen 17, semitransparent paper such as, for example, tracing paper can be used.

Photoelectric converters 19 are disposed at suitable positions on the opposite side of the filtering screen 17 from the pipe 14. The output signals from the photoelectric converters 19 are treated by a signal treating means 20. Since the surface of the filtering screen 17 is rough, a leveled optical image is obtained.

In the embodiment shown in FIG. 3, a photoelectric converter 19b is disposed near the position of the filtering screen 17 and away from a position having a high degree of brightness which is produced by a sound portion of the surface of the material 14. Thus, the method according to the present invention permits extensively detecting the component of the beam which is scattered due to flaws on the surface of the metal material. FIG. 4 shows an example of a signal obtained by this embodiment, having pulse-like positive signals indicating that the quantity of light in the beam has increased indicating the presence of flaws on the surface of the material.

Further, since the photoelectric converter 19a is disposed in a central position having the highest brightness, the changes in intensity of the directly reflected beam can be detected and the condition of the polished surface of the material can be known.

As shown in FIG. 5, a plurality of photoelectric converters 19a, 19b, 19c, 19d, ... may be disposed around a position 21 having the highest brightenss on the opposite side of a filtering screen 17, and in suitable positions near the position 21, so as to enable a comparison of a plurality of signals from the photoelectric converters with one another to obtain various information on the flaws on the surface of the material, for example, not only sizes and positions but also types of flaws.

The present invention is directed to a method of detecting flaws on the surface of a metal material as described hereinbefore, in which the beam reflected or scattered by the surface of the metal is leveled by using a reflecting screen or a filtering screen having a rough surface. Consequently, the present invention prevents disturbance due to the changes in the surface condition of the sound portion of the surface of the material and due to the vibrations of the metal material occurring when it is moved from adversely affecting the detection of flaws. Unlike the conventional method in which a directly reflected beam is detected, the present invention achieves an improvement in the S/N ratio and permits accurately detecting flaws on the surface of metal material as well as information as to the sizes and positions thereof.

It is to be realized that only preferred embodiments of the invention have been disclosed and that numerous modifications, substitutions and alterations are all permissible without departing from the spirit and scope of the invention as defined in the following claims.

What is claimed is:

1. A method of detecting flaws on the surface of a metal material, comprising:
   directing a laser beam onto the surface of the metal material to be inspected for varying the position of impingement;
   passing the component of the beam which is directly reflected by the surface of the metal material and the component of the beam which is scattered by the surface of the metal material through a semitransparent filter having a rough surface; and
   separately measuring the changes in the quantity of light in said components of the reflected beam and the scattered beam and using the changes thus measured for detecting the presence of flaws on the surface of the metal material.

2. The method according to claim 1, wherein the step of separately measuring the changes in the quantity of light in the components passing through said filter comprises measuring the quantity of light by separate photoelectric converters spaced from each other.

3. The method according to claim 1 wherein the step of measuring the changes in the quantity of light in the directly reflected component comprises measuring the changes in the quantity of light with a first photoelectric converter, and the step of measuring the changes in the quantity of light in the scattered component comprises measuring the changes in the quantity of light with a plurality of photoelectric converters, and said step of using said changes comprises comparing the output signals from the firstmentioned photoelectric converter with the outputs of said plurality of photoelectric converters.

4. The method according to claim 3 in which said firstmentioned photoelectric converter is in a first position and the converters of said plurality of photoelectric converters are positioned around said firstmentioned converter.

5. A method of detecting flaw on the surface of a metal material, comprising:

directing a laser beam onto the surface of the metal material to be inspected for varying the position of impingement;

reflecting the directly reflected component of the laser beam which is reflected from the surface of the metal material from a reflector having a rough surface; and measuring the change in the quantity of light in the beam reflected from said reflector and using the changes in the measuring quantities of light for detecting the presence of flaws on the surface of the metal material.

6. The method according to claim 5 in which the step of measuring the changes in the quantity of light in the beam reflected from the reflector comprises measuring the quantity of light by a photoelectric converter.

* * * * *